(12) United States Patent
Frigg

(10) Patent No.: US 9,161,791 B2
(45) Date of Patent: Oct. 20, 2015

(54) BONE PLATE

(75) Inventor: Robert Frigg, Bettlach (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2362 days.

(21) Appl. No.: 12/017,666

(22) Filed: Jan. 22, 2008

(65) Prior Publication Data
US 2008/0132955 A1 Jun. 5, 2008

Related U.S. Application Data

(63) Continuation of application No. 10/695,392, filed on Oct. 29, 2003, now Pat. No. 7,354,441, which is a continuation of application No. 09/994,050, filed on Nov. 27, 2001, now Pat. No. 6,669,701, which is a continuation of application No. PCT/CH00/00037, filed on Jan. 27, 2000.

(51) Int. Cl.
*A61B 17/80* (2006.01)

(52) U.S. Cl.
CPC ......... *A61B 17/8014* (2013.01); *A61B 17/8052* (2013.01); *A61B 17/8061* (2013.01); *A61B 17/8057* (2013.01)

(58) Field of Classification Search
CPC ............... A61B 17/80; A61B 17/8014; A61B 17/8052; A61B 17/8057
USPC ............. 606/280, 281, 283, 284, 70, 71, 291, 606/316, 289
See application file for complete search history.

(56) References Cited

U.S. PATENT DOCUMENTS

| | | | |
|---|---|---|---|
| 3,552,389 A * | 1/1971 | Allgower et al. | 606/282 |
| 3,596,656 A | 8/1971 | Kaute | |
| 3,668,972 A | 6/1972 | Allgower et al. | |
| 3,716,050 A * | 2/1973 | Johnston | 606/286 |
| 3,779,240 A * | 12/1973 | Kondo | 606/282 |
| RE28,841 E | 6/1976 | Allgower et al. | |
| 4,219,015 A | 8/1980 | Steinemann | |

(Continued)

FOREIGN PATENT DOCUMENTS

| | | |
|---|---|---|
| DE | 4341980 | 6/1995 |
| DE | 4343117 | 6/1995 |

(Continued)

OTHER PUBLICATIONS

Medikit Product Catalogue, 2008, Eastern Medikit Limited, India, www.orthomedikit.com, 34 sheets.

(Continued)

*Primary Examiner* — Zade Coley
(74) *Attorney, Agent, or Firm* — Fay Kaplun & Marcin, LLP

(57) ABSTRACT

A bone plate includes an upper surface, a bone contacting surface, and at least one hole extending through the upper and bone contacting surfaces for receiving a bone screw. The at least one hole includes a first portion and a second portion that overlap one another. The first portion defines a substantially circular outer periphery and the second portion defines an elongated outer periphery that is elongated in a direction substantially parallel to the longitudinal axis of the plate. The first portion may have threads configured to engage threads on the head of a bone screw, and the second portion may be configured to cooperate with the head of a different bone screw to provide compression to the fracture.

19 Claims, 4 Drawing Sheets

(56) References Cited

U.S. PATENT DOCUMENTS

| | | | |
|---|---|---|---|
| 4,338,926 A | 7/1982 | Kummer et al. | |
| 4,408,601 A | 10/1983 | Wenk | |
| RE31,628 E | 7/1984 | Allgower et al. | |
| 4,493,317 A | 1/1985 | Klaue | |
| 4,513,744 A | 4/1985 | Klaue | |
| 4,565,193 A | 1/1986 | Streli | |
| 4,838,252 A | 6/1989 | Klaue | |
| 4,927,421 A | 5/1990 | Goble et al. | |
| 4,957,497 A | 9/1990 | Hoogland | |
| 4,988,350 A | 1/1991 | Herzberg | |
| 5,002,544 A | 3/1991 | Klaue et al. | |
| 5,006,120 A | 4/1991 | Carter | |
| 5,041,114 A | 8/1991 | Chapman et al. | |
| 5,085,660 A | 2/1992 | Lin | |
| 5,129,901 A | 7/1992 | Decoste | |
| 5,151,103 A | 9/1992 | Tepic et al. | |
| 5,190,544 A | 3/1993 | Chapman et al. | |
| 5,197,966 A | 3/1993 | Sommerkamp | |
| 5,269,784 A | 12/1993 | Mast | |
| 5,275,601 A * | 1/1994 | Gogolewski et al. | 606/291 |
| 5,304,180 A | 4/1994 | Slocum | |
| 5,324,290 A | 6/1994 | Zdeblick et al. | |
| 5,364,398 A | 11/1994 | Chapman et al. | |
| 5,364,399 A | 11/1994 | Lowery et al. | |
| 5,569,251 A * | 10/1996 | Baker et al. | 606/281 |
| 5,601,553 A * | 2/1997 | Trebing et al. | 606/86 B |
| 5,702,399 A | 12/1997 | Kilpela et al. | |
| 5,709,686 A * | 1/1998 | Talos et al. | 606/281 |
| 5,810,823 A | 9/1998 | Klaue et al. | |
| 5,938,664 A | 8/1999 | Winquist et al. | |
| 6,139,550 A * | 10/2000 | Michelson | 606/70 |
| 6,183,475 B1 | 2/2001 | Lester et al. | |
| 6,206,881 B1 * | 3/2001 | Frigg et al. | 606/291 |
| 6,322,562 B1 * | 11/2001 | Wolter | 606/62 |
| 6,364,882 B1 | 4/2002 | Orbay | |
| 6,440,135 B2 | 8/2002 | Orbay et al. | |
| 6,454,769 B2 | 9/2002 | Wagner et al. | |
| 6,454,770 B1 | 9/2002 | Klaue | |
| 6,527,776 B1 | 3/2003 | Michelson | |
| D479,331 S | 9/2003 | Pike et al. | |
| 6,623,486 B1 | 9/2003 | Weaver et al. | |
| 6,669,701 B2 | 12/2003 | Steiner et al. | |

FOREIGN PATENT DOCUMENTS

| | | | |
|---|---|---|---|
| DE | 4438264 | 3/1996 | |
| DE | 9321544 | 9/1999 | |
| EP | 0207884 | 1/1987 | |
| EP | 1468655 | 10/2004 | |
| FR | 2233973 | 1/1975 | |
| FR | 2405062 | 5/1979 | |
| FR | 2405705 | 5/1979 | |
| FR | 2405706 | 5/1979 | |
| FR | 2496429 | 6/1982 | |
| SU | 1279626 | 12/1986 | |
| WO | WO 9709000 A1 * | 3/1997 | A61B 17/80 |
| WO | 0053110 | 9/2000 | |
| WO | 0053111 | 9/2000 | |

OTHER PUBLICATIONS

Statement of Case by M/S Eastern Medikit Limited re: Application to revoke Indian Patent No. 195986, Jan. 31, 2008, 15 sheets.

Affidavit of Shri Mohinder Paul, Apr. 2, 2008, 13 sheets.

Counterstatement of the Respondent to the Revocation Claim re: Indian Patent No. 195986 Filed by Petitioner; Jul. 19, 2008, 24 sheets.

ACE Symmetry (TM) Titanium Upper Extremity Plates, ACE Medical Company, 2000, 4 sheets.

* cited by examiner

BONE PLATE

CROSS-REFERENCE TO RELATED APPLICATIONS

The present application is a Continuation of Application of U.S. patent application Ser. No. 10/695,392 filed on Oct. 29, 2003 which is a Continuation Application of Ser. No. 09/994,050 U.S. Pat. No. 6,669,701 issued Dec. 30, 2003 which is a Continuation of PCT Patent Application Serial No. PCT/CH2000/000037 filed Jan. 27, 2000. The disclosures of these applications is incorporated herein by reference.

TECHNICAL FIELD OF THE INVENTION

The present invention relates generally to devices for fixation of parts of a fractured bone and more specifically, to bone plates and systems for stabilization and/or compression of parts of a fractured bone.

BACKGROUND OF THE INVENTION

Bone plates may generally be utilized to carry out two different types of osteosynthesis, namely "rigid osteosynthesis" and "flexible osteosynthesis." Rigid osteosynthesis is used for medical care of joint fractures, simple shaft fractures (where nailing is impossible) as well as for osteotomies. Aside from the possibility of anatomical repositioning, the bone itself supports and stabilizes the osteosynthesis, which allows for the possibility of putting stress on the extremity earlier and without pain. Additional advantages of the medical care of stable fractures can be observed when the blood circulation in the bone is greatly diminished due to trauma. For treating "nonunions" or in the case of existing infection, the fracture must be kept stable in order to make bone healing possible and so as not to irritate the infection further by instability of the fracture gap.

Flexible osteosynthesis, also known as "biological osteosynthesis," may be desirable in the medical treatment of comminuted fractures in the shaft region of tubular bones. In the case of these fractures, it is an objective to maintain the proper length of the bone and to fix the bone ends (joints) in their proper anatomic positions with respect to one another. With flexible osteosynthesis, the fracture zone is not directly affixed or manipulated, and consequently, the blood circulation in this area is not inhibited. Bone plates designed for flexible osteosynthesis thus operate similarly to a locking, intramedullary nail, which is anchored only in the metaphyses.

Since fractures cannot always be treated with one type of osteosynthesis, surgeons must frequently compromise because a bone plate, which allows him to combine the two types of osteosynthesis discussed above, is not available. Such a combination would be beneficial, for example, when a joint fracture can be compressed with traction screws through the bone plate and the whole of the joint may be connected to the diaphysis over an internal fixative with angularly stable screws. Another illustrative application concerns porotic bones, where a bone plate with axially and angularly stable screws can be anchored in the metaphysial fragment, with a stable plate-affixation being undertaken in the diaphyseal range with the assistance of a plate traction screw through the fracture. A primary fracture stabilization can be achieved by this type of procedure.

This situation has led to the development and marketing of bone implants for both types of osteosynthesis. The two types of implants, however, are designed specifically for their respective method. Thus, the disadvantages of these two systems lie in the difficulty in combining them.

Thus, a need exists for improved bone plates that provide for both rigid and flexible osteosynthesis.

SUMMARY OF THE INVENTION

The present invention is directed to a bone plate that is adapted to be used for both rigid and flexible osteosynthesis, without compromising the ability of the plate to be used for either type of osteosynthesis. Accordingly, the bone plate of the present invention may be used as a compression plate or as an internal fixative.

This objective is accomplished with a bone plate having at least one "combination hole." The combination hole may be used with a screw having a substantially spherical head to provide for compression of the fracture, or may be used with a screw having a threaded head to fix the position of the screw with respect to the bone plate and serve as an internal fixative.

The combination hole includes a first portion and a second portion that at least partially overlap one another. The first portion may be substantially circular, and the second portion may be elongated. Within the scope of the invention, the second portion (elongated portion) may have a diametrical dimension that is greater in one direction than in another. For example, the diameter of the elongated portion may be greater in the direction of the longitudinal axis of the plate than in the direction substantially perpendicular to the longitudinal axis. Thus, the elongated portion may be oval, elliptical, rectangular or any other elongated shape known to one of ordinary skill in the art, including combinations of these shapes. The diameter (D) of the first portion (circular portion) may be smaller than the minor (or shortened) axis (B) of the second portion (elongated portion). Typically, diameter (D) is between about 5% and about 25% smaller than the minor axis (B).

According to another aspect of the invention, the circular portion of the hole may be configured and dimensioned to engage the head of a bone screw. More specifically, the circular portion may be provided with an internal thread or a peripheral lamella or lip that may engage a corresponding structure formed on the screw-head. In the case where an internal thread is provided, the thread may be disposed in a single plane, or in several planes. The plane(s) may be parallel to the upper and/or bone contacting surfaces of the bone plate. According to one embodiment, the internal thread may extend over the whole height of the bone plate from the bone contacting surface to the upper surface. This configuration provides increased stability of the bone plate/screw-head interface.

With the threaded screw-head engaged in the threads of the first portion, the bone plate may be used as an internal fixative. Use in this configuration, however, creates high stresses at the interface of the bone plate and screw-head because the plate is not forced against the bone, and therefore, the bone fracture is fixed primarily by friction between the plate and the bone. This increase in stress is taken into account by the threaded portion of the hole extending over a range of at least about 180° with respect to a central axis of the hole, and thereby enclosing the screw-head in at least this angular range. This feature of the bone plate is especially advantageous where thin bone plates are involved. Preferably, the threaded portion is disposed on one of the two longitudinal ends of the hole. This positioning allows for the threaded portion to extend over a larger angular range. For example, the threaded portion may extend over a range of between about 190° and about 280°, and preferably over a range of between about 200° to 250°, thus maximizing the strength of the bone screw to bone plate interface.

According to another embodiment of the invention, the internal thread may be tapered (i.e., formed on the inner surface of a hole that tapers with respect to its central axis). Preferably, the internal thread tapers radially inward toward the bone contacting surface of the bone plate. A bone screw to be rigidly fixed to the bone plate may include a screw-head having a tapered external thread (i.e., formed on an outer surface of the screw-head that tapers with respect to the central axis of the screw-head) that is tapered to match the shape of the tapered internal thread. The bone screw may be rigidly fixed to the bone plate by engagement between the matching threads. This method of attachment is especially advantageous when self-drilling screws are to be used since, due to the tapered shape of the matching threads, the screw may be inserted into the bone independently of the plate. More specifically, the screw-head becomes rigidly clamped to the plate only as the threaded screw-head penetrates the threaded portion of the hole. Despite any initial misalignment between the threads on the screw-head (the position of which are initially dictated by the orientation of the bone screw in the bone) and the threads on the bone plate, the tapered shape of the mating threads ensures that the threads on the screw-head will ultimately align with the threaded portion of the hole. When the tapered thread of the screw-head is tightened into the internal thread of the hole, the screw-head creates radial forces in the plate hole. Thus, the bone plate must be dimensioned and configured to withstand these high radial forces, e.g., to withstand flexing of the walls of the screw holes in the bone plate.

According to one embodiment, the inner thread conically tapers at a cone angle of between about 5° and about 20°. Preferably, the thread tapers at a cone angle of about 10°.

In the case where the inner thread is tapered, as discussed above, the thread may extend through a different angle when measured at the upper surface than when measured at the bone contacting surface. For example, when measured at the upper surface, the inner thread may extend through a first angle of between about 180° and about 230°, while when measured at the bone contacting surface, the inner thread may extend through a second angle of between about 230° and about 270°.

The first portion of the hole, and consequently the inner thread (if provided), may be oriented closer to the center or intermediate portion (as distinguished from the ends) of the plate than the second portion, thus avoiding any undesirable effects on the compression capability of the second portion. Thus, when the bone plate is used as a compression plate, the geometry of the second portion (compression portion) is not adversely affected by the presence of the internal thread.

According to another aspect of the present invention, at least one of the holes may be dimensioned and configured to receive a substantially spherical head of a bone screw and provide for compression of the fractured bone fragments. For example, according to one embodiment, the second portion of the elongated hole, discussed above, may include a concave, substantially spherical recess at the upper surface. The recess may be dimensioned and configured to accommodate the spherical head of a conventional bone screw. Such an arrangement may be especially useful when the bone screw is put in place eccentrically with respect to the hole, as is necessary for attaining compression of a fracture. Additionally, the second portion of the hole may flare outward in the area of the bone contacting surface to provide for increased angulation of the bone screw with respect to the bone plate.

According to another embodiment of the invention, the underside of the bone plate may be concave, thus allowing the plate to conform to the rounded cross-section of the tibia, femur, humerus, forearm bone, and other bones with which the present invention may be used. The concave configuration of the underside also allows a conventional bone screw to be inserted obliquely through the plate hole. This feature may be especially important when gripping a small bone fragment, which must be pulled against the plate.

The present invention is also directed to a bone plating system including at least one bone screw. The bone screw may have a screw-head that is configured and dimensioned to engage the circular portion of the above-described combination hole. For example, the screw-head may include a plurality of external threads disposed thereon that engage the internal threads of the bone plate.

BRIEF DESCRIPTION OF THE DRAWINGS

To facilitate an understanding of the characteristics, structure and operation of the invention, preferred features of the invention are described in the accompanying discussion, wherein similar reference characters denote similar elements throughout the several views or embodiments, and wherein.

DETAILED DESCRIPTION OF THE PREFERRED EMBODIMENTS

Figure 1:
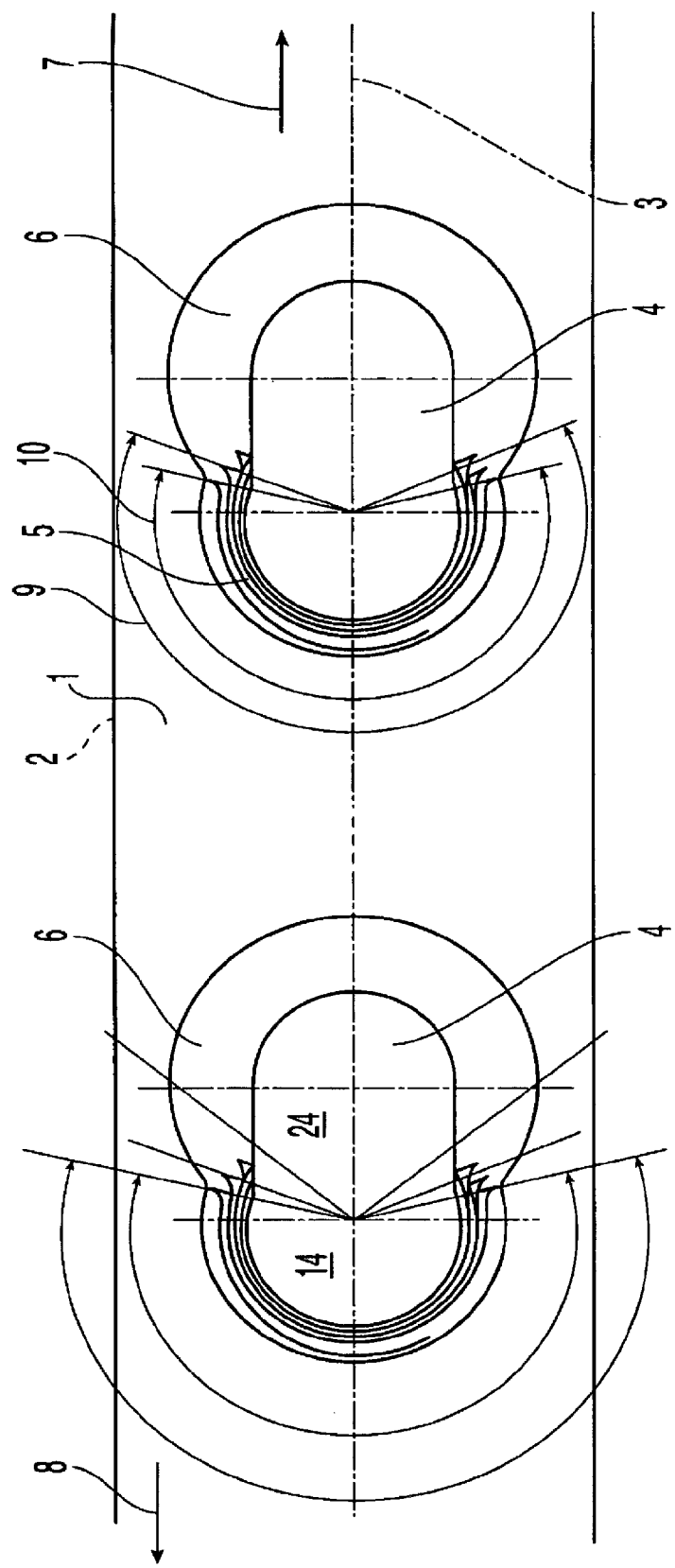
FIG. 1 is a top view of a segment of an illustrative embodiment of a bone plate according to the present invention.
Figure 2:
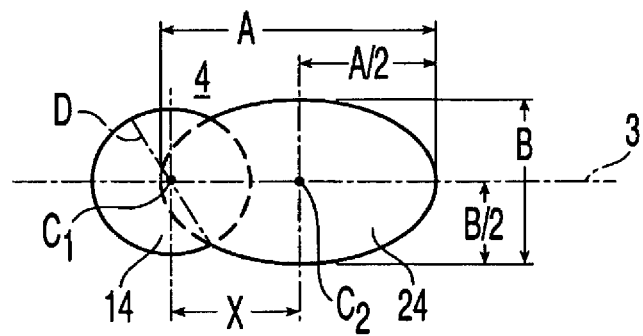
FIG. 2 is a schematic representation of a combination hole of the bone plate of FIG. 1.

One embodiment of a bone plate according to the present invention is shown in FIG. 1. The bone plate defines a longitudinal axis 3, and includes an upper surface 1 and a bone contacting surface 2 intended for contact with the bone. At least one combination hole 4 extends through the upper surface 1 and the bone contacting surface 2. Hole 4 may receive a bone screw 11 that is used to hold the bone plate on the fractured bone. While two holes 4 are shown, the bone plate may be provided with any number of holes 4 as may be suitable for a specific surgical application. In addition, holes 4 may be disposed along the longitudinal axis 3 as shown in FIG. 2, however, holes 4 may alternatively be spaced from the longitudinal axis 3. One of ordinary skill in the art will know and appreciate that the bone plate may be provided with other types and configurations of holes in addition to combination hole 4. For example, the bone plate may be provided with substantially cylindrical holes, threaded holes, or any other type of hole known to one of ordinary skill in the art. The arrow 7 indicates the direction toward one end of the plate, while the arrow 8 indicates the direction toward the center of the plate.

As shown schematically in FIG. 2, the combination hole 4 consists of a first, substantially circular portion 14, and a second, elongated portion 24. The circular portion 14 and the elongated portion 24 overlap one another, and are thus in communication with one another. The outer periphery of circular portion 14 defines a first center point $C_1$, and a diameter D. The outer periphery of elongated portion 24 defines a second center point $C_2$. The outer periphery of elongated portion 24 also defines a major axis A and a minor axis B substantially perpendicular to the major axis A. According to one embodiment of the invention, major axis A may be substantially parallel to longitudinal axis 3 of the bone plate. In addition, major axis A may lie on longitudinal axis 3 with first and second center points $C_1$, $C_2$ located on longitudinal axis 3, however other configurations are possible.

Still referring to FIG. 2, first center point $C_1$ and second center point $C_2$ are separated from one another by a distance X, which may be less than the sum of D/2 and A/2. Preferably, distance X satisfies the following condition:

$$0.5(D/2+A/2)<X<1.0(D/2+A/2)$$

According to another embodiment, diameter D is less than minor axis B. Preferably, diameter D satisfies the following condition:

$$0.75B \leq D \leq ~0.95B$$

Figure 3:
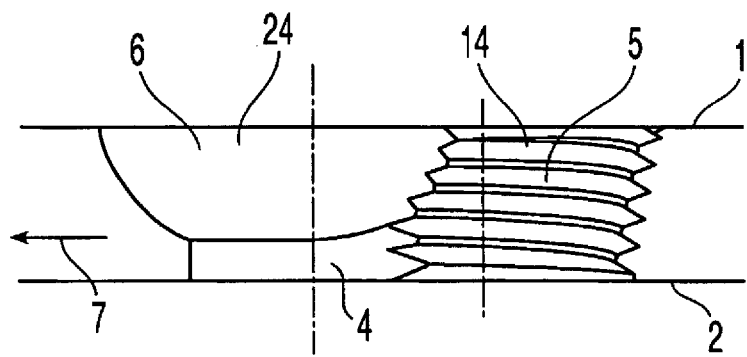
FIG. 3 is a longitudinal cross-sectional view of a portion of the bone plate of FIG. 1, taken through one of the combination holes.

Elongated portion 24 may be configured and dimensioned to receive a substantially spherical screw-head. As shown in FIGS. 1 and 3, elongated portion 24 may have a concave, substantially spherical recess 6 that opens toward upper surface 1 of the bone plate. When the shaft of a bone screw having a spherical head is located eccentrically in elongated portion 24 (towards the left in FIG. 3), the spherical head may engage recess 6 and bias the bone plate to provide compression of the bone fracture.

Still referring to FIG. 3, circular portion 14 may be configured and dimensioned to engage a threaded head of a bone screw. As shown, an internal thread 5 may be provided on circular portion 14. Thread 5 may be disposed in a single plane, or in several planes. The plane(s) may be parallel to upper surface 1 and/or bone contacting surface 2. According to the embodiment shown, thread 5 extends substantially over the entire height of the bone plate from the upper surface 1 to the bone contacting surface 2. In the case where thread 5 is provided, it is preferably oriented at the end of hole 4 that is closest to the center of the bone plate.

With reference to FIG. 1, when measured at upper surface 1, thread 5 extends over a first angle 9 of about 256° with respect to center $C_1$ of circular portion 14, and when measured at bone contacting surface 2, thread 5 extends over a second angle 10 of about 223° with respect to center point $C_1$. One of ordinary skill in the art will know and appreciate, however, that other values of first angle 9 and second angle 10 are possible.

The table below displays, for illustrative purposes only, preferred parameters which may be used for thread 5.

| | | | |
|---|---|---|---|
| Thread Diameter [mm] | 2.4 | 3.5 | 5.0 |
| Double Thread | Yes | Yes | Yes |
| Lead [mm] | 0.6 | 0.8 | 1.0 |
| Thread Depth [mm] (defined as approximately half the difference between the external and internal thread) | 0.175 | 0.2295 | 0.2810 |
| Angular Range (at upper surface) | 200° | 200° | 190° |
| Angular Range (at bone contacting surface) | 260° | 204° | 250° |

Figure 5:
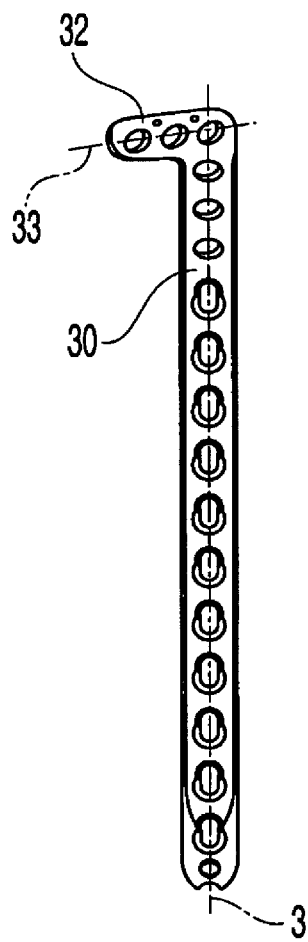
FIG. 5 is a top view of a substantially L-shaped bone plate according to the present invention.
Figure 6:
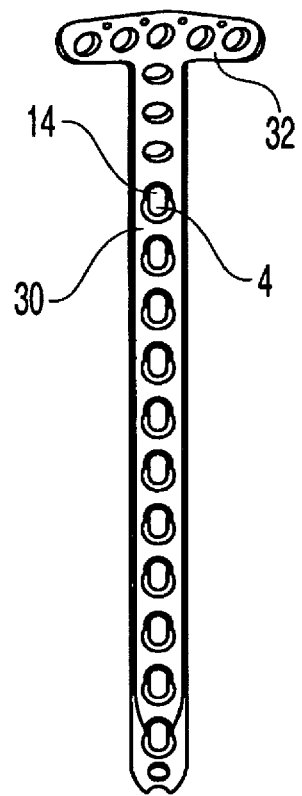
FIG. 6 is a top view of a substantially T-shaped bone plate according to the present invention.
Figure 7:
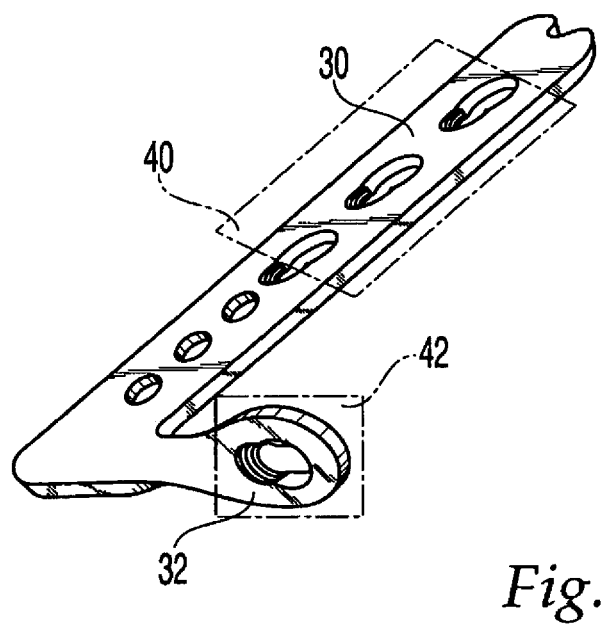
FIG. 7 is a perspective view of the bone plate of FIG. 5.

The bone plate may include multiple sections having longitudinal axes that are oriented with respect to one another in order to fit a particular medical application. Referring now to FIG. 5, according to one embodiment, the bone plate may include a first section 30 that, as described above, has a first longitudinal axis 3, and a second section 32 that similarly has a second longitudinal axis 33. As shown, the first and second longitudinal axes 3, 33 may be angled with respect to one another. In addition, the first and second sections 30, 32 may have different lengths, e.g., the first section may be longer than the second section. For example, the bone plate may be substantially T-shaped, as shown in FIG. 6, or L-shaped, as shown in FIG. 5, although other configurations are possible. The sections may also be located in different planes. For instance, as shown in FIG. 7, the plate may be bent or twisted such that the bone contacting surface of the first section 30 is located in a first plane 40 and the bone contacting surface of the second section 32 is located in a second plane 42 different from the first plane 40. This may be beneficial where the bone plate has to be located over a curved portion of a bone, such as the femoral head.

In the case where one section is longer than another, at least one combination hole 4 is preferably located on the longer section and oriented with the first portion 14 of the hole 4 located closer to the shorter section than the second portion 24 of the hole 4. Thus, in the case of a T-shaped plate, shown in FIG. 6, the hole 4 would preferably be disposed on the first, longer section 30 of the plate with the first portion 14 oriented closer to the second, shorter section 32.

Figure 4:
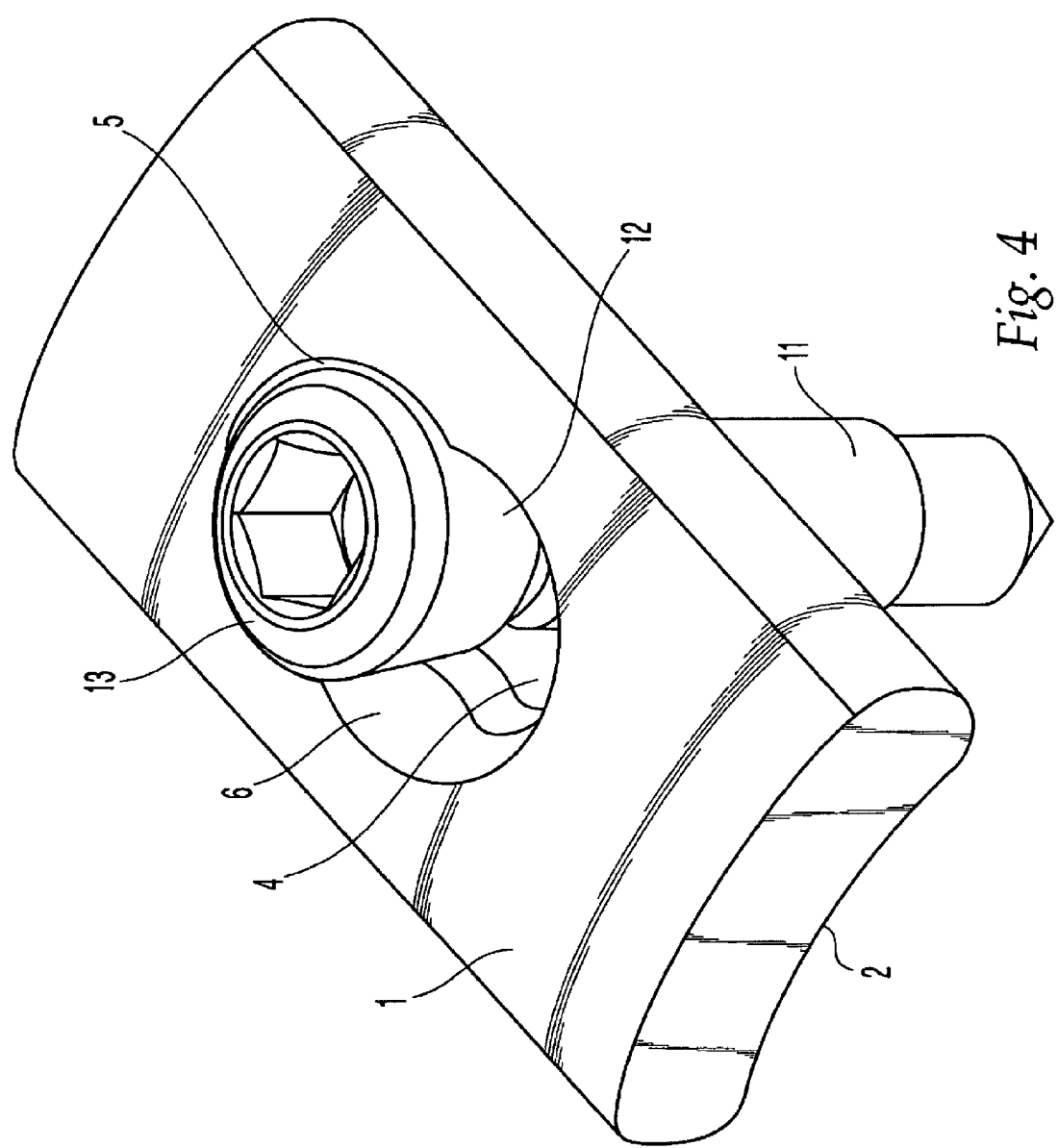
FIG. 4 is a perspective view of a portion of the bone plate of FIG. 1, shown with a bone screw inserted in one of the combination holes.

Referring to FIG. 4, combination hole 4 is shown with a bone screw 11 received therein. The head 13 of the bone screw 11 preferably has one or more threads 12 disposed thereon. Threads 12 of the bone screw 11 may mate with threads 5 of hole 4, to fix the position of bone screw 11 with respect to plate 4. Preferably, bone screw 11 is self-drilling and/or self-tapping.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed:

1. A bone plate, comprising:
a first fixation element receiving hole extending therethrough from an outer surface to a bone facing surface of the plate, the first hole including a first substantially circular segment defining a first segment axis and at least one thread for engaging a head of a fixation element inserted therethrough, the at least one thread extending along a wall of the first segment over an angle of at least 180° with respect to the first segment axis and a second segment open to the first segment, a length of the second segment in a direction parallel to a longitudinal axis of the plate being longer than a diameter of the first segment and longer than a width of the second segment in a direction substantially perpendicular to the longitudinal axis, the width of the second segment being longer than the diameter of the first segment.

2. The bone plate of claim 1, wherein the at least one thread includes a plurality of thread segments, each of the thread segments extending along a portion of a path corresponding to a path of a thread of a fixation element to be received therein, the thread segments being separated from one another at the opening from the first segment to the second segment.

3. The bone plate of claim 2, wherein the plurality of thread segments taper radially inward in a direction from the outer surface toward the bone facing surface.

4. The bone plate of claim 1, wherein first and second ends of the second segment are separated from one another along the longitudinal axis, a distance between the first segment axis and the first end of the second segment being greater than a distance between the first and second ends of the second segment.

5. The bone plate of claim 1, wherein a wall of the second segment is substantially elliptical.

6. The bone plate of claim 1, wherein a portion of a wall of the second segment is angled to engage an angled head of a fixation element inserted therethrough so that contact between the head and the angled portion of the wall provide compression of fractured bone fragments coupled to the plate.

7. The bone plate of claim 1, wherein a segment axis connecting a first center point of the first segment and a second center point of the second segment is substantially parallel to the longitudinal axis.

8. The bone plate of claim 7, wherein the segment axis is co-linear with the longitudinal axis.

9. The bone plate of claim 7, wherein the segment axis is spaced from the longitudinal axis.

10. The bone plate of claim 7, further comprising:
a second hole including a first substantially circular segment defining a first segment axis and at least one thread for engaging a head of a fixation element inserted therethrough, the at least one thread extending along a wall of the first segment over an angle of at least 180° with respect to the first segment axis and a second segment open to the first portion, a length of the second segment in a direction parallel to a longitudinal axis of the plate being longer than a diameter of the first segment and longer than a width of the second segment in a direction substantially perpendicular to the longitudinal axis.

11. The bone plate of claim 1, further comprising:
a cross portion extending substantially transverse to the longitudinal axis.

12. The bone plate of claim 11, wherein the plate is one of substantially T-shaped and substantially L-shaped.

13. The bone plate of claim 11, wherein the first segment of the first hole is closer to the cross portion than is the second segment of the first hole.

14. The bone plate of claim 1, wherein the bone facing surface is concave.

15. The bone plate of claim 1, further comprising:
a second substantially circular hole including a wall extending around an entire circumference thereof.

16. The bone plate of claim 1, further comprising:
a second elongated hole having a length in a direction parallel to the longitudinal axis greater than a width in a direction substantially perpendicular to the longitudinal axis, a wall of the second elongated hole enclosing an entire periphery thereof.

17. The bone plate of claim 1, wherein a diameter of the first segment decreases in a direction from the outer surface to the bone facing surface.

18. The bone plate of claim 17, wherein the decrease in diameter of the first segment defines a taper angle of between 5° and 20°.

19. The bone plate of claim 1, wherein at least one thread extends along the wall of the first segment over an angle of between 180° and 230° with respect to the first segment axis.

* * * * *